US00PP28020P3

(12) United States Plant Patent
Castellarin et al.

(10) Patent No.: US PP28,020 P3
(45) Date of Patent: May 16, 2017

(54) GRAPEVINE NAMED 'MERLOT KANTHUS'

(50) Latin Name: *Vitis×vinifera (hybrid)*
Varietal Denomination: MERLOT KANTHUS

(71) Applicants: Università degli Studi di Udine, Udine UD (IT); Istituto di Genomica Applicata, Udine UD (IT)

(72) Inventors: Simone Diego Castellarin, Vancouver (CA); Guido Cipriani, Faedis (IT); Gabriele Di Gaspero, Cividale del Friuli UD (IT); Michele Morgante, Tricesimo UD (IT); Enrico Peterlunger, Codroipo UD (IT); Raffaele Testolin, Udine (IT)

(73) Assignees: Università degli Studi di Udine, Udine (IT); Istituto di Genomica Applicata, Udine (IT)

( * ) Notice: Subject to any disclaimer, the term of this patent is extended or adjusted under 35 U.S.C. 154(b) by 0 days.

(21) Appl. No.: 14/545,114

(22) Filed: Mar. 27, 2015

(65) Prior Publication Data

US 2016/0242337 P1 Aug. 18, 2016

(30) Foreign Application Priority Data

Feb. 13, 2015 (QZ) ..... PBR 2015/0365

(51) Int. Cl.
*A01H 5/08* (2006.01)

(52) U.S. Cl.
USPC ..... Plt./205

(58) Field of Classification Search
USPC ..... Plt./205
See application file for complete search history.

*Primary Examiner* — Annette Para
(74) *Attorney, Agent, or Firm* — Foley & Lardner LLP

(57) ABSTRACT

A new and distinct variety of grapevine named 'MERLOT KANTHUS', primarily adapted to the growing conditions of the temperate regions, and characterized by its medium vigor; erect growth habit; medium sized, circular shaped leaves; small, conical, medium dense berry clusters with two middle size wings; blue-black berries with slightly firm flesh, none to herbaceous taste and none to very weak flesh coloration; primary use for wine; and resistance to winter temperatures (to −22° C.), resistance to downy mildew, and tolerance to powdery mildew.

4 Drawing Sheets

Latin name of the genus and species of the plant claimed: *Vitis×vinifera* (hybrid).

Variety name: 'MERLOT KANTHUS'.

BACKGROUND OF THE INVENTION

The present invention relates to a new and distinct summer/fall bearing grapevine variety, botanically known as *Vitis vinifera*, and hereinafter referred to by the name 'MERLOT KANTHUS'.

The new grapevine 'MERLOT KANTHUS' is a product of a controlled breeding program conducted by the inventors in Udine, Italy. The objective of the breeding program was to deyelop a new grapevine variety particularly characterized by resistance to cold (<−20° C.), resistance to downy mildew (*Plasmopara viticola*), and tolerance to powdery mildew (*Uncinula necator*).

The new grapevine 'MERLOT KANTHUS' originated from a cross made by the inventors in 2002 in Udine, Italy. The female or seed parent is the grapevine variety, *Vitis vinifera* cv. 'Merlot' (unpatented), and the male or pollen parent is the grapevine variety, *Vitis* cv. '20/3' (Bianca× SK77-4/5) (unpatented).

The new grapevine 'MERLOT KANTHUS' was discovered and selected by the inventors as a single flowering plant within the progeny of the stated cross in a controlled environment in 2002 in Udine, Italy. Asexual reproduction of the new grapevine variety by grafting was first performed in February 2004 in Rauscedo, Friuli Venezia Giulia region, Italy, and has demonstrated that the combination of characteristics as herein disclosed for the new cultivar are firmly fixed and retained through successive generations of asexual reproduction. The new cultivar reproduces true to type.

SUMMARY OF THE INVENTION

'MERLOT KANTHUS' is primarily adapted to the climate and growing conditions of the temperate regions with average yearly temperature about 13° C., minimum winter temperature about −20° C., annual rainfall around 700-1500 mm of rain (e.g. North-Eastern Italy, Friuli). This region provides the necessary year-round temperatures required for it to produce and maintain a strong vigorous plant with consistent fruit production from April through November on primocanes and in the ensuing year from April through November on the floricanes.

The following traits have been repeatedly observed and are determined to be unique characteristics of 'MERLOT KANTHUS', which in combination distinguish this grapevine plant as a new and distinct variety.

1. Medium vigor;
2. Erect growth habit;
3. Medium sized, circular shaped leaves with medium to medium green upper surfaces and light green lower surfaces and medium texture;
4. Small, conical, medium dense berry clusters with two middle size wings; blue-black berries with slightly firm flesh, none to herbaceous taste, and none to very weak flesh coloration; primarily used for wine and maturing in early September (Middle Friuli, North-Eastern Italy);

5. Primocanes and floricanes with a circular cross section, brownish colour, no lenticels, and short-medium internodes (diameter 8 mm);
6. Harvesting time in early September (Middle Friuli, North-Eastern Italy); and
7. Resistance to winter temperature (−22° C.), resistance to downy mildew, and tolerance to powdery mildew.

Plants of the new grapevine 'MERLOT KANTHUS' differ from plants of the parents, *Vitis vinifera* 'Merlot' (unpatented) and *Vitis* cross '20/3' (unpatented), in the following characteristics described in Table 1.

TABLE 1

Comparison with parent varieties

| Characteristic | New Cultivar 'MERLOT KANTHUS' | Female Parent 'Merlot' (unpatented) | Male Parent '20/3' (unpatented) |
|---|---|---|---|
| vigor: growth habit | medium erect | medium horizontal | medium semi-erect |
| leaf | small to medium, medium to dark green color (upper surface), light green color (lower surface), no hairs in both surfaces, wedge shape, medium texture, | medium, dark green color (upper surface), green color (lower surface), very few hairs in both surfaces, wedge shape, medium texture | Medium size, light green color (upper surface), green color (lower surface), no hairs in both surfaces, wedge-shaped—kidney-shaped, medium texture |
| cluster | low weight, conical with two middle size wings, loose or medium dense, berry skin with blue blackcolour, soft flesh, neutral taste, no flesh coloration | low weight, long, with 1-2 wings, medium, berry skin with blue black color, soft flesh, neutral taste, no flesh coloration | low weight, conical, with 1-2 wings, medium dense, berry skin with green-yellow color, slightly firm flesh, neutral taste, no flesh coloration |
| primocane and floricane | circular cross section, brownish colour, lenticels: absent, short-medium internodes, diameter: small (about 8 mm) | circular cross section, brownish color, lenticels: absent, short-medium internodes, diameter small (about 8 mm) | oblate cross section, brownish color, lenticels: absent, medium internodes, diameter small (about 8 mm) |
| harvesting time | First decade September(Middle Friuli, North-Eastern Italy), | Early-medium early September (Middle Friuli, North-Eastern Italy) | Early (end August, Middle Friuli, North-Eastern Italy) |
| resistances | resistant to winter temperature (−22° C.), resistant to downy resistant to downy mildew, tolerant to powdery mildew. | Average resistance to winter temperature (−22° C.), very low resistance to downy mildew, very low resistance to powdery mildew | resistant to winter temperature not checked, resistant to downy mildew, resistant to powdery mildew |

Of the many commercial cultivars known to the present inventor, the most similar to the new grapevine 'MERLOT KANTHUS' is the female parent 'Merlot', to which a comparison has been provided above.

BRIEF DESCRIPTION OF THE PHOTOGRAPHS

The accompanying photographs illustrate the overall appearance of the new grapevine 'MERLOT KANTHUS' showing the colors as true as is reasonably possible with colored reproductions of this type. Colors in the photographs may differ slightly from the color values cited in the detailed botanical description, which accurately describe the color of 'MERLOT KANTHUS'.

DETAILED BOTANICAL DESCRIPTION

Figure 1A:
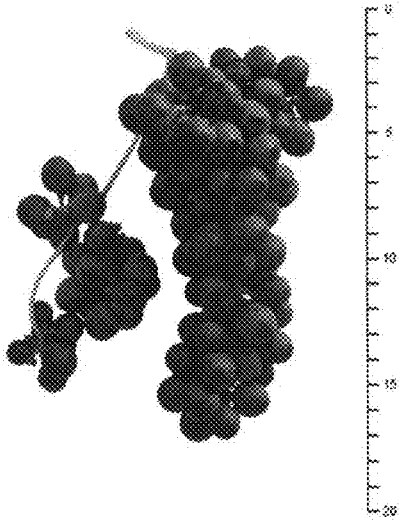
FIG. 1A and FIG. 1B show a typical fruit cluster of 'MERLOT KANTHUS' taken on Sep. 9, 2012, in Udine, Italy.
Figure 1B:
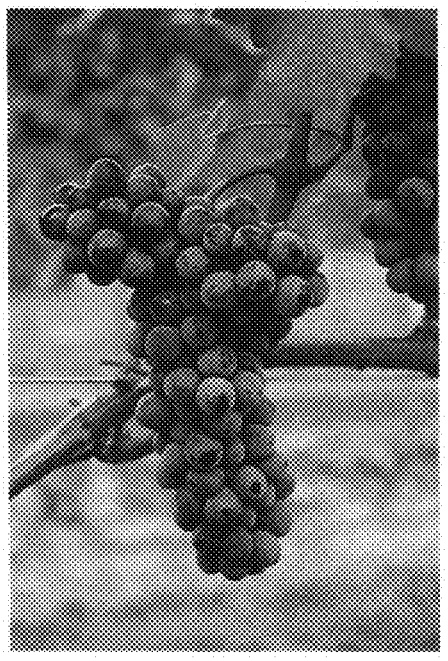
Figure 2:
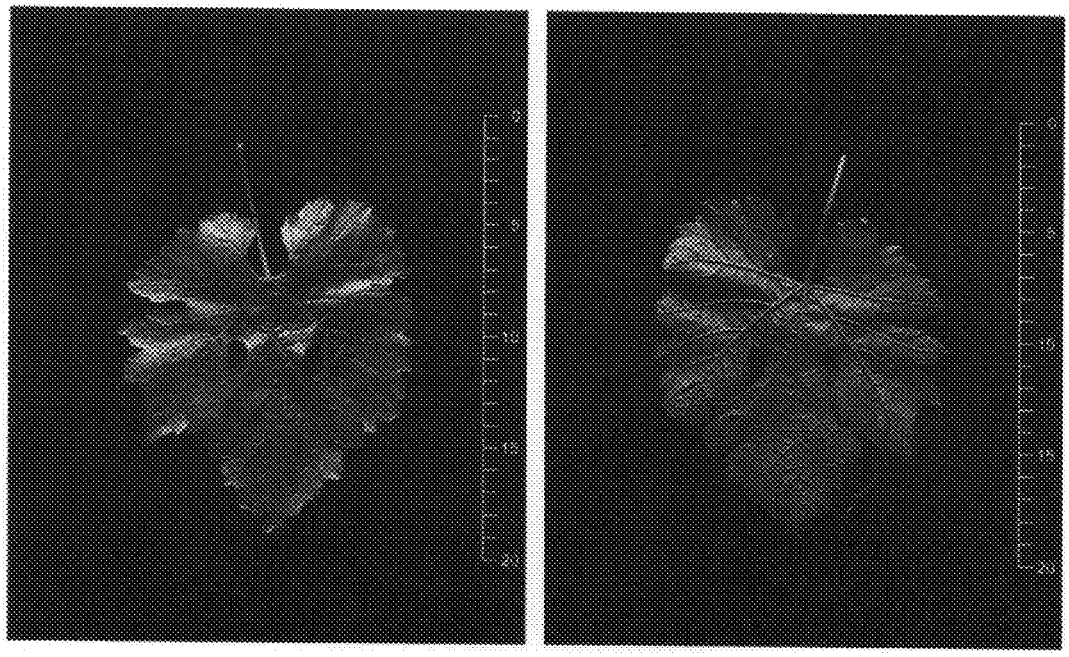
FIG. 2 shows a typical mature leaf (upper surface, left and lower surface, right) of 'MERLOT KANTHUS' taken on May 31, 2012, in Udine, Italy.
Figure 3:
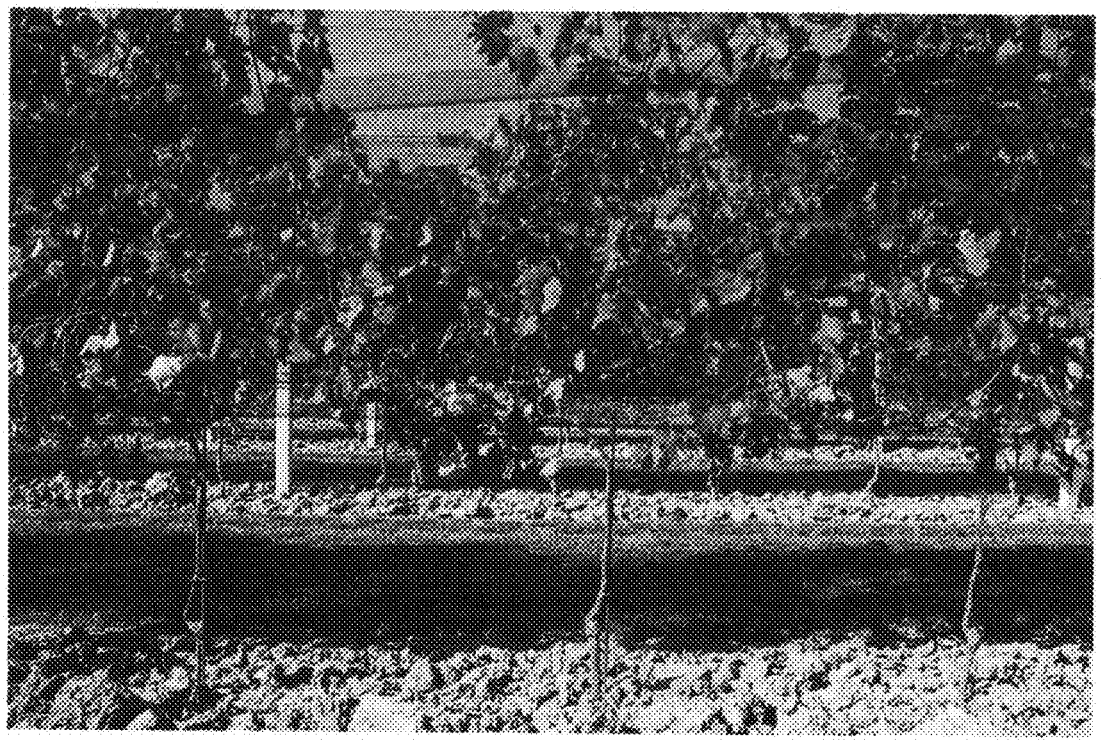
FIG. 3 shows a typical mature vine of 'MERLOT KANTHUS' taken on Aug. 3, 2012.
Figure 4:
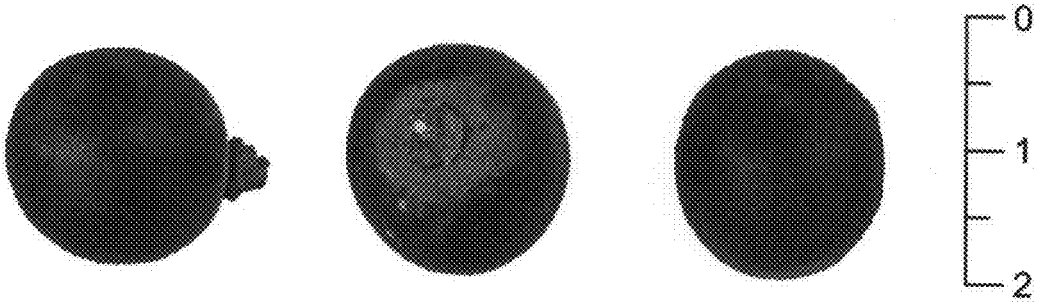
FIG. 4 shows a close-up view of typical mature fruit of 'MERLOT KANTHUS' taken on Sep. 9, 2012, in Udine, Italy.

The following description of 'MERLOT KANTHUS' unless otherwise noted, is based on observations taken during the 2011, 2012, and 2013 growing seasons(s) in Udine, Italy and Fossalon di Grado (GO), Italy, from plants dug from a nursery located in Rauscedo (PN), Italy during the beginning of December 2007 and planted approximately 16 to 20 weeks later in Udine, Italy and Fossalon di Grado (GO), Italy. The phenotypical descriptions and color designations stated for the new variety may vary, depending upon variations in environmental factors, including weather (temperature, humidity and light intensity), day length, soil type, location and cultural conditions. 'MERLOT KANTHUS' has not been observed under all possible environmental conditions.

Color references are made to The Royal Horticultural Society Colour Chart (R.H.S.), (Edition V, 2007), except where general colors of ordinary significance are used.

| Characteristic | 'MERLOT KANTHUS' | 'Merlot' (unpatented) |
|---|---|---|
| GENERAL | | |
| Resistance to pest/disease | Resistant to downy mildew, tolerant to powdery mildew | Susceptible to downy mildew and to powdery mildew |
| Resistance to natural elements | Resistant to winter cold down to −23° C. | Resistant to winter cold down to −22° C. |
| VINE | | |
| Vigor | medium | medium |
| Trunk diameter | 6 cm (6 yrs-old plant) | 6 cm (6 yrs-old plant) |
| Bark | | |
| color | RHS 177B | Dark brown |
| underbark color | RHS 179B | Light brown |
| texture | n.a. | n.a. |
| Canes | | |
| length | Internode length cm 10.5 | Internode length about cm 10 |
| width | 8 mm | 8 mm |
| Shoots | | |
| shape | Erected, cross section: circular, surface: with stripes, nodes and internodes without hairs | Horizontal, cross section: circular, surface: smooth, nodes and internodes without hairs |
| color | internodes with red (RHS 185B) and green | Internodes with green colour on ventral and |

-continued

| Characteristic | 'MERLOT KANTHUS' | 'Merlot' (unpatented) |
|---|---|---|
| | (RHS 144B) pigmentation on both sides, nodes with red (RHS 185B) and green (RHS 144B) dorsal side and green (RHS 144B) ventral side | dorsal side, nodes with green ventral and dorsal side |
| Tendrils | | |
| form | Bifid or trifid | bifid |
| color | RHS 143B | Green |
| texture | normal | normal |
| number | 2 or <2 consecutive | 2 or <2 consecutive |
| Buds | | |
| size | average | average |
| shape | round | round |
| color | RHS 139C and RHS181A | Light brown |
| number | 2/node | 2/node |
| time of budbreak | early | early-medium |
| LEAVES | | |
| Size | medium | medium |
| Number of leaflets | n.a. | n.a. |
| Glossiness | Medium | medium |
| Cross section shape | Twisted | Flat |
| Color (immature) | | |
| Upper surface | RHS 140B and RHS 185B | Light green |
| Under surface | RHS 1408 and RHS 185B | green |
| Color (mature) | | |
| Upper surface | RHS 143B | Dark green |
| Under surface | RHS 143C | green |
| Petiole | | |
| Length (cm) | 6.2 | 6.0 |
| Color (upper surface) | RHS 145B and RHS 184D | green |
| Color (under surface) | RHS I45C and RHS 184D | green |
| Stipule orientation | n.a. | n.a. |
| FLOWERS | | |
| Flowering period (time of beginning of flowering) | Early June | Early June |
| Sex | hermaphrodite | hermaphrodite |
| Size | Average | average |
| Diameter (cm) | 0.3 (stamens) | 0.3 (stamens) |
| Stamen color | RHS 4D | |
| Pistil color | RHS 149A | |
| Fragrance | n.a. | n.a. |
| Flower number (at 3rd node from tip of lateral mean and range) | n.a. | n.a. |

-continued

| Characteristic | 'MERLOT KANTHUS' | 'Merlot' (unpatented) |
|---|---|---|
| Petals | | |
| Length (cm) | n.a. | n.a. |
| Width (cm) | n.a. | n.a. |
| Overall shape | calyptra | calyptra |
| Calyptra Color | RHS 134A | green |
| Sepals | | |
| Length (cm) | n.a. | n.a. |
| Width (cm) | n.a. | n.a. |
| Overall shape | n.a. | n.a. |
| Color (immature) | n.a. | n.a. |
| Upper surface | | |
| Under surface | | |
| Color (mature) | n.a. | n.a. |
| Upper surface | | |
| Under surface | | |
| Pedicel | | |
| Length (mm) | 45 (cluster) | 45 |
| Color | RHS 145C | green |
| FRUIT | | |
| Primocane time of fruiting (1st pick) | September 6th | September 7th |
| Clusters | | |
| cluster weight | Low (g 160) | Low (g 160) |
| cluster shape | conical | conical |
| cluster length | mm 170 | medium |
| avg. berries per cluster | 180 | 180 |
| avg. clusters per shoot | 2 | 2 |
| Berries | | |
| Berry size | g 1.67 | g 1.80 |
| Berry length (cm) | 1.60 | 1.50 |
| Berry width (cm) | 1.60 | 1.50 |
| Overall shape of berry | broad ellipsoid | Broad ellipsoid |
| Berry Texture | soft | soft |
| Berry Skin Color (immature) | RHS 137C | green |
| Berry Skin Color (mature, at 19° Bx) | RHS 99A | Blue black |
| Berry Flesh Color | RHS 148B | |
| Soluble solids (%) | 22.4 | 22.0 |
| Titratable acidity (as g/L tartaric acid) | 5.1 | 5.5 |
| Sugar/acid ratio | 4.4 | 4.0 |
| Firmness | soft | soft |
| Seeds | 2-3 | 2-3 |
| Seed color | RHS 163A and RHS 106B | |
| Skin cracking? | no | rarely |
| Juice color | transparent | transparent |
| Berry taste | Neutral | neutral |
| Eating quality | n.a. | n.a. |
| Berry uses | wine | wine |
| Shipping quality | n.a. | n.a. |

What is claimed is:

1. A new and distinct grapevine, referred to as 'MERLOT KANTHUS', as herein described and illustrated by the characteristics set forth above.

* * * * *